United States Patent
Conley (10) Patent No.: US 11,564,720 B2
(45) Date of Patent: Jan. 31, 2023

(54) INTRAMEDULLARY STABILIZATION SCREW

(71) Applicant: Acumed LLC, Hillsboro, OR (US)

(72) Inventor: Brian Conley, Portland, OR (US)

(73) Assignee: Acumed LLC, Hillsboro, OR (US)

( * ) Notice: Subject to any disclaimer, the term of this patent is extended or adjusted under 35 U.S.C. 154(b) by 0 days.

(21) Appl. No.: 17/195,112

(22) Filed: Mar. 8, 2021

(65) Prior Publication Data

US 2021/0282822 A1 Sep. 16, 2021

Related U.S. Application Data

(60) Provisional application No. 62/988,127, filed on Mar. 11, 2020.

(51) Int. Cl.
*A61B 17/72* (2006.01)
*A61B 17/86* (2006.01)

(52) U.S. Cl.
CPC ...... *A61B 17/7291* (2013.01); *A61B 17/7283* (2013.01); *A61B 17/8645* (2013.01)

(58) Field of Classification Search
CPC . A61B 17/72; A61B 17/7291; A61B 17/7283; A61B 17/86; A61B 17/863; A61B 17/8645; A61B 17/8625; F16B 5/0275
USPC .......................................... 411/412, 413, 415
See application file for complete search history.

(56) References Cited

U.S. PATENT DOCUMENTS

| | | | | |
|---|---|---|---|---|
| 3,861,269 A | * | 1/1975 | Laverty | F16B 25/0057 411/413 |
| 5,259,398 A | * | 11/1993 | Vrespa | A61C 8/0025 411/413 |
| 2005/0107791 A1 | * | 5/2005 | Manderson | A61B 17/7216 606/62 |
| 2014/0012334 A1 | * | 1/2014 | Armstrong | A61B 17/863 606/312 |
| 2014/0025124 A1 | * | 1/2014 | Champagne | A61B 17/86 606/311 |
| 2016/0030097 A1 | * | 2/2016 | Mildner | A61B 17/863 606/304 |
| 2017/0196609 A1 | * | 7/2017 | Champagne | A61B 17/7291 |
| 2017/0348033 A1 | * | 12/2017 | Varner | A61B 17/8605 |
| 2019/0262047 A1 | * | 8/2019 | Sommers | A61B 17/8875 |
| 2020/0022817 A1 | * | 1/2020 | Crossgrove | A61B 17/8625 |

(Continued)

*Primary Examiner* — Eduardo C Robert
*Assistant Examiner* — Michelle C Eckman
(74) *Attorney, Agent, or Firm* — K&L Gates LLP (57) ABSTRACT

A bone screw for intramedullary fixation of hand or foot bones comprises three sections of a threaded distal portion, a threaded center portion and a threaded proximal portion. The threaded distal portion comprises a first full thread with a first constant diameter and a first constant pitch throughout the threaded distal portion, wherein an open end of the threaded distal portion forms a leading end of the bone screw. The threaded center portion comprises a second full thread with a second constant diameter and a second constant pitch throughout the threaded center portion, wherein the second constant diameter is the same as the first constant diameter, and the second constant pitch is smaller than the first constant pitch. The threaded proximal portion comprises a third full thread with a third constant diameter and a third constant pitch throughout the threaded proximal portion.

18 Claims, 8 Drawing Sheets

(56) References Cited

U.S. PATENT DOCUMENTS

2020/0085477 A1* 3/2020 Blitz .................. A61B 17/8625
2020/0237415 A1* 7/2020 Champagne ....... A61B 17/8645

* cited by examiner

INTRAMEDULLARY STABILIZATION SCREW

PRIORITY CLAIM

The present application claims priority to and the benefit of U.S. Provisional Application 62/988,127, filed Mar. 11, 2020, the entirety of which is herein incorporated by reference.

BACKGROUND OF THE INVENTION

1. Field of the Invention

The subject disclosure relates to surgical implants for intramedullary fixation of bones in the hands or feet and more, specifically, bone screws or orthopedic bone screws for stabilization of metacarpals or metatarsals.

2. Background of the Related Art

Bones in the hands and feet, such as metacarpals and metatarsals, have a unique hourglass-shaped intramedullary canals within such bones. The existing bone screws often do not provide satisfactory fixation on the proximal and distal ends of these bones as the intramedullary canals are much larger on the ends (cancellous bones) in comparison to the center isthmus (i.e., cortical bone).

Therefore, there remains a need to solve the problems in the art pertaining to orthopedic operation on a hand or foot bone fracture. More particularly there is a need to solve the challenges associated with orthopedic screw fixation or stabilization. Further, there is a need to provide a bone screw that meets most or all of the design requirements of the surgeon, most particularly, fully engaging both the proximal and distal ends and the center of the hand or foot bone.

SUMMARY

The present disclosure provides a bone screw for intramedullary fixation of hand or foot bones. In an example, the provided bone screw includes a threaded distal portion, a threaded center portion, and a threaded proximal portion. The threaded distal portion includes a first thread with a first constant diameter and a first constant pitch throughout the threaded distal portion. An open end of the threaded distal portion forms a leading end of the bone screw. The threaded center portion includes the first thread and a second thread. The threaded center portion has a second constant diameter and a second constant pitch throughout the threaded center portion. The second constant diameter is the same as the first constant diameter, and the second constant pitch is smaller than the first constant pitch. The threaded proximal portion includes the first thread with the first constant diameter and the first constant pitch throughout the threaded proximal portion. An open end of the threaded proximal portion forms a driving end of the bone screw. The first thread has the first constant diameter and the first constant pitch throughout the threaded distal portion, the threaded center portion, and the threaded proximal portion.

In some aspects, the bone screw can be headless. In other aspects, the bone screw can include a head. In various aspects, the threaded distal portion, the threaded center portion, and the threaded proximal portion can be fully threaded. The second or third constant pitch of the bone screw can be one half or one third of the first constant pitch. In one embodiment, the second or third constant pitch of the bone screw can be $1/N$ ($N \geq 4$) of the first constant pitch. For example, the second or third constant pitch of the bone screw can be one fourth, one fifth, one sixth, one seventh, one eighth, one ninth, one tenth, and so on of the first constant pitch.

The threaded center portion of the bone screw includes a greater number of threads than the threaded distal portion and the threaded proximal portion. For example, the threaded center portion may include two or three threads while the threaded distal portion and the threaded proximal portion each include a single thread. The threaded center portion may include any suitable quantity of thread revolutions. For example, the threaded center portion of the bone screw may include 4, 6, 8, 10, 12, 14, 16, 18 or more thread revolutions.

Similarly, each of the threaded distal portion and the threaded proximal portion of the bone screw can comprise any suitable quantity of thread revolutions that fit in the threaded distal portion or in the threaded proximal portion. For example, each of the threaded distal portion and the threaded proximal portion of the bone screw can include 1, 2, 3, 4, 5, 6, 7, 8, 9 or more thread revolutions.

In some aspects, at least part of the threaded distal portion the bone screw is self-tapping. The bone screw can be used for intramedullary fixation of metacarpals or metatarsals. A size of the first constant diameter of the bone screw is such that the bone screw fits in an intramedullary canal of a hand or foot bone. The hand or foot bone can be either a metacarpal or a metatarsal.

The threaded proximal portion and the threaded distal portion of the bone screw can engage cancellous bones of either end of the metacarpal or the metatarsal, and the threaded center portion of the bone screw can engages an isthmus, in the center of the metacarpal or the metatarsal.

The present disclosure also provides for a method for treating a bone fracture. The example method may include inserting into a patient, through an incision in a foot or a hand bone of the patient, a bone screw. The bone screw includes a threaded distal portion, a threaded center portion, and a threaded proximal portion. The threaded distal portion is configured and adapted for insertion into an intramedullary canal of a first cancellous bone section of the foot or the hand bone. The threaded center portion is configured and adapted for insertion into the intramedullary canal of an isthmus bone section of the foot or the hand bone. The threaded proximal portion is configured and adapted for insertion into the intramedullary canal of a second cancellous bone section of the foot or the hand bone.

Each of the threaded distal portion and the threaded proximal portion can have a first constant diameter and a first constant pitch. The threaded center portion can have a second constant diameter and a second constant pitch throughout the threaded center portion. The second constant diameter is the same as the first constant diameter, and the second constant pitch is smaller than the first constant pitch.

In one embodiment, the second constant pitch of the bone screw can be $1/N$ ($N \geq 4$) of the first constant pitch. For example, the second constant pitch of the bone screw can be one fourth, one fifth, one sixth, one seventh, one eighth, one ninth, one tenth, and so on of the first constant pitch.

The provided method may further include adjusting the position of the bone screw within the intramedullary canal so that the threaded proximal portion and the threaded distal portion of the bone screw engage cancellous bones of either end of the foot or the hand bone, and the threaded center portion of the bone screw engages an isthmus, in the center of the foot or the hand bone.

These and other features of the subject invention and the manner in which it is manufactured and employed will become readily apparent to those having ordinary skill in the art from the following enabling description of the embodiments of the subject invention taken in conjunction with the several drawings described below.

BRIEF DESCRIPTION OF THE DRAWINGS

So that those having ordinary skill in the art to which the present disclosure pertains will more readily understand how to employ the devices and methods of the present disclosure, embodiments thereof will be described in detail herein below with reference to the drawings, wherein.

These and other aspects of the subject disclosure will become more readily apparent to those having ordinary skill in the art from the following detailed description of the invention taken in conjunction with the drawings.

DETAILED DESCRIPTION

Disclosed herein are detailed descriptions of specific embodiments of surgical implants for intramedullary fixation of bones in the hands and/or feet. The disclosed embodiments are merely examples of the way in which certain aspects of the invention may be implemented and do not represent an exhaustive list of all of the ways the invention may be embodied. Indeed, it will be understood that the systems, devices and methods described herein may be embodied in various and alternative forms. Moreover, the figures are not necessarily to scale and some features may be exaggerated or minimized to show details of particular components.

Well-known components, materials or methods are not necessarily described in great detail in order to avoid obscuring the present disclosure. Any specific structural and functional details disclosed herein are not to be interpreted as limiting, but merely as a basis for the claims and as a representative basis for teaching one skilled in the art to variously employ the invention. Moreover, the devices, instruments and implants are described herein as being used for intramedullary fixation of hand or foot bones, but those skilled in the art will appreciate that they can be used in other medical procedures.

Currently, there lacks an orthopedic bone screw designed to better engage the unique bone structure of intramedullary canals in the hand and/or foot bones such as metacarpals and metatarsals. For example, the existing bone screws often do not provide satisfactory fixation on the proximal and distal ends of these bones, as the intramedullary canals are much larger on the ends (cancellous bones) than in the center isthmus (i.e., cortical bone).

Embodiments herein provide for a single bone screw with three distinct sections to target and fully engage both cancellous bones on the ends of these bones and the isthmus (i.e., cortical bone) in the center of these bones. For example, the threads (e.g., thread profiles and thread pitches) of a distal portion and a proximal portion of the bone screw are specifically designed to fully engage and secure cancellous bone on both ends of these bones. Additionally, the threads (e.g., thread profiles, thread pitches and number of thread leads) of a center portion are specifically designed to include a higher density of thread revolutions to better support the isthmus (i.e., cortical bone) in the center of these bones. As such, stability of the bone screw within intramedullary canals may be significantly improved as compared to typical bone screws.

The present disclosure now will be described more fully, but not all embodiments of the disclosure are necessarily shown. In addition, many modifications may be made to adapt a particular situation or material to the teachings of the disclosure without departing from the essential scope thereof.

Figure 1:
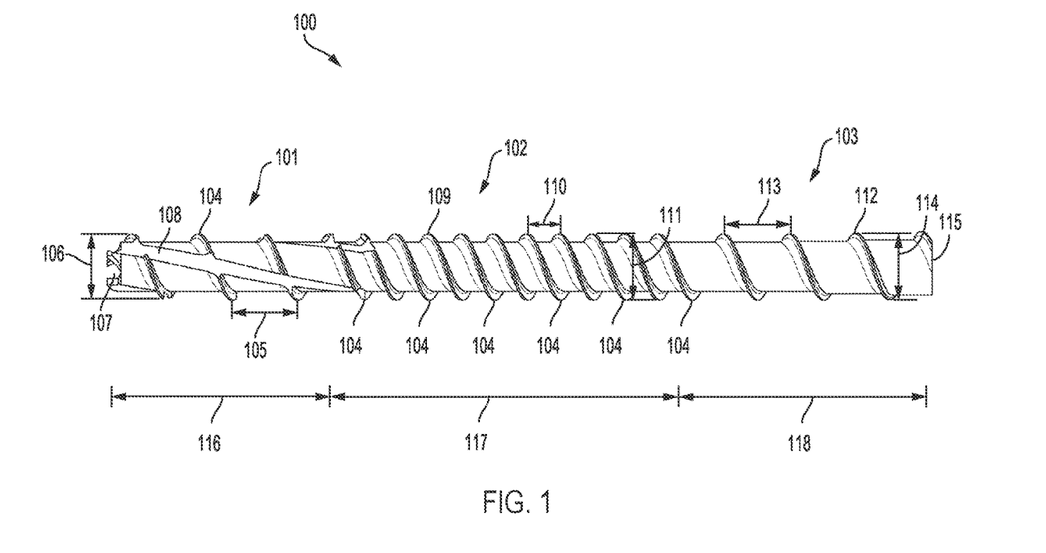
FIG. 1 illustrates a perspective view of a bone screw, according to an aspect of the present disclosure.

Referring to the figures, FIG. 1 shows an illustrative bone screw 100 according to an embodiment herein. As show in FIG. 1, the bone screw 100 includes three portions: a threaded distal portion 101; a threaded center portion 102; and a threaded proximal portion 103. The threaded distal portion 101 has a thread 104 with multiple revolutions within the threaded distal portion 101, though in some aspects the thread 104 may only have a single revolution within the threaded distal portion 101. In one embodiment, the threaded distal portion 101 is fully threaded with the thread 104. In some aspects, the bone screw 100 may be headless as illustrated. In other aspects, the bone screw 100 may include a head.

In one embodiment, the threaded distal portion 101 has a constant core diameter (not shown) throughout the threaded distal portion 101. In one embodiment, the thread 104 has a constant outside diameter 106 throughout the threaded distal portion 101. In one embodiment, the thread 104 has a constant pitch 105 in the threaded distal portion 101.

In one embodiment, an open end 107 of the threaded distal portion 101 forms a leading end of the bone screw 101. For example, the threaded distal portion 101 can include self-tapping portion 108, which can help the bone screw 100 better cut into a hand or foot bone.

The bone screw 100 is adapted to fit within the intramedullary canals of a hand and/or foot bone, such as a metacarpal or a metatarsal. When the bone screw 100 is inserted within an intramedullary canal of a hand or foot bone, the threaded distal portion 101 is arranged on the bone screw 100 such that the threaded distal portion 101 can engage cancellous bone within the intramedullary canal.

In various aspects, the whole length 116, the constant outside diameter 106, the profile of the thread 104, and/or the constant pitch 105 of the threaded distal portion 101 can be adapted to fit within an intramedullary canal and fully engage cancellous bone of either end of a hand or foot bone, such as a metacarpal or a metatarsal.

In an example, a surgeon might first examine a hand or foot bone of a patient to determine a suitable length, outside diameter, profile of threads and/or thread pitch of a bone screw. The suitable whole length 116, constant outside diameter 106, profile of the thread 104, and/or constant pitch 105 of the threaded distal portion 101 may then be determined on the basis of a specific hand or foot bone of a specific patient.

It is well known that a hand or foot bone, such as metacarpals and metatarsals, includes intramedullary canals with a unique hourglass shape within the bone. Thus, the intramedullary canal is larger on both the ends than in the center isthmus. As such, it is difficult for a surgeon to get a good bone fixation on both the ends with existing bone screws.

In one embodiment, the bone screw 100 is specifically designed to fully engage cancellous bone on both ends of the bone screw 100 while also engaging the isthmus in the center of the bone screw 100. For example, the threaded distal portion 101 and the threaded proximal portion 103 may be adapted such that the bone screw 100 fully engages cancellous bone on either end of the bone screw 100 and the threaded central portion 102 is adapted such that the bone screw 100 fully engages the isthmus in the center of the bone screw 100.

As shown in FIG. 1, the center portion of the bone screw 100 is the threaded center portion 102. In some aspects, the threaded center portion 102 may be double-threaded. For example, the threaded center portion 102 includes multiple revolutions of the thread 104 and multiple revolutions of a thread 109. In one embodiment, the threaded center portion 102 is fully threaded with the thread 104 and the thread 109. In other aspects, the threaded center portion 102 may be triple-threaded (e.g., the example bone screw 400 of FIGS. 4 and 5) or include more than three threads.

In one embodiment, the threaded center portion 102 has a constant core diameter (not shown) throughout the threaded center portion 102. In one embodiment, the thread 109 has a constant outside diameter 111 throughout the threaded center portion 102. In one embodiment, the constant outside diameter 111 of the thread 109 is the same as the constant outside diameter 106 of the thread 104.

In one embodiment, the threaded center portion 102 has a constant pitch 110. The constant pitch 110 for the threaded center portion 102 is smaller than the constant pitch 105 of the threaded distal portion 101. As such, the threaded center portion 102 has a greater density of the revolutions of the thread 104 and the thread 109 as compared to the density of the revolutions of the thread 104 for the threaded distal portion 101. In at least some aspects, the thread 109 may have a constant pitch equal to the constant pitch 105.

In one embodiment, the constant pitch 110 for the threaded center portion 102 may be ½, ⅓, ¼, ⅕, ⅙, ⅐, ⅛, ⅑, ⅒, 1/11, 1/12, etc. of the constant pitch 105 of the threaded distal portion 101. For example, FIG. 1 shows that the constant pitch 110 for the threaded center portion 102 is ½ of the constant pitch 105 of the threaded distal portion 101. FIG. 1 further shows that the thread 104 is continuous between the threaded distal portion 101 and the threaded center portion 102. Stated differently, the thread 104 is a single thread that extends through both the threaded distal portion 101 and the threaded center portion 102.

Within the intramedullary canals of a hand or foot bone, such as a metacarpal or a metatarsal, the threaded center portion 102 of the bone screw 100 would align with, and fully support, cortical bone (i.e., isthmus) in the center.

The greater density of thread revolutions (e.g., smaller pitch) in the threaded center portion 102 as compared with the threaded distal portion 101 helps provide additional support for the bone screw 100 to secure the isthmus in the center of the intramedullary canal.

In one embodiment, the threaded distal portion 101 of the bone screw 100 can comprise any suitable quantity of thread revolutions that fit in the threaded distal portion 101. For example, the threaded distal portion 101 of the bone screw can include 1, 2, 3, 4, 5, 6, 7, 8, 9, etc. revolutions of the thread 104.

In some aspects, the threaded distal portion 101 of the bone screw 100 may include more than one thread (e.g., more than the thread 104). In such aspects, the threaded center portion 102 includes a greater quantity of threads than the threaded distal portion 101.

In one embodiment, the threaded center portion 102 of the bone screw 100 can include any suitable quantity of thread revolutions that fit in the threaded center portion 102. For example, the threaded center portion 102 of the bone screw 100 can include 4, 6, 8, 10, 12, 14, 16, 18 or more revolutions of the thread 104 and the thread 109.

In one embodiment, the threaded center portion 102 of the bone screw 100 may include 6 or more revolutions of the thread 104 and the thread 109.

In one embodiment, the threaded center portion 102 of the bone screw 100 may include 8 or more revolutions of the thread 104 and the thread 109.

In one embodiment, the threaded center portion 102 of the bone screw 100 may include 10 or more revolutions of the thread 104 and the thread 109.

In one embodiment, the threaded center portion 102 of the bone screw 100 may include 12 or more revolutions of the thread 104 and the thread 109.

In one embodiment, the threaded center portion 102 of the bone screw 100 may include 16 or more revolutions of the thread 104 and the thread 109.

In at least some aspects, the parameters of the threaded center portion 102—the whole length 117, the constant outside diameter 111, the profile of the thread 104 and the thread 109, and/or the constant pitch 110—are adapted to fit within an intramedullary canal and fully engage cortical bone (i.e., isthmus) of the center of a hand or foot bone, such as a metacarpal or a metatarsal. For example, a surgeon might first examine a hand or foot bone of a patient to determine a suitable length, outside diameter, profile of threads and/or thread pitch of a bone screw. The suitable whole length 117, constant outside diameter 111, profile of the thread 104 and the thread 109, and/or constant pitch 110 of the threaded center portion 102 may then be determined on the basis of a specific hand or foot bone of a specific patient.

As shown in FIG. 1, the bone screw 100 also includes the threaded proximal portion 103. The threaded proximal portion 103 includes multiple revolutions of a thread 112. In one embodiment, the threaded proximal portion 103 is fully threaded with the thread 112.

In at least some aspects, the thread 112 is the thread 104. Stated differently, in such aspects, the thread 104 is a single, continuous thread that extends throughout the threaded distal portion 101, the threaded center portion 102, and the threaded proximal portion 103.

In one embodiment, the threaded proximal portion 103 has a constant core diameter (not shown) throughout the threaded proximal portion 103. In one embodiment, the thread 112 has a constant outside diameter 114 throughout the threaded proximal portion 103. In one embodiment, the constant outside diameter 114 is equal to the constant outside diameter 111 of the threaded center portion 102.

In another embodiment, the core diameter (not shown) of the threaded proximal portion 103 is not constant throughout the threaded proximal portion 103. For example, the core diameter (not shown) of the threaded proximal portion 103 can increase or decrease towards the proximal (driver) end 115 of the bone screw 100.

In one embodiment, the constant outside diameter 114 for the threaded proximal portion 103, the constant outside diameter 111 for the threaded center portion 102, and the constant outside diameter 106 for the threaded distal portion 101 are all equal. As such, the bone screw 100 has a uniform outside diameter throughout in this embodiment.

In another embodiment, one or more of the outside diameter 114 for the threaded proximal portion 103, the outside diameter 111 for the threaded center portion 102, and the outside diameter 106 for the threaded distal portion 101 are not constant. For example, any of the outside diameter 114 for the threaded proximal portion 103, the outside diameter 111 for the threaded center portion 102, and the outside diameter 106 for the threaded distal portion 101 can increase or decrease along the bone screw 100.

In one embodiment, the thread 112 of the threaded proximal portion 103 has a constant pitch 113. In some aspects, the constant pitch 113 for the threaded proximal portion 103 is equal to the constant pitch 105 of the thread 104 of the threaded distal portion 101.

In at least some embodiments, the constant pitch 113, the constant pitch 105 and the constant pitch 110 enable the thread 104 to extend continuously through the threaded distal portion 101, the threaded center portion 102, and the threaded proximal portion 103.

In various aspects, the whole length 118, the constant outside diameter 114, the profile of the thread 112, and/or the constant pitch 113 of the threaded proximal portion 103 can be adapted to fit within an intramedullary canal and fully engage cancellous bone of either end of a hand or foot bone, such as a metacarpal or a metatarsal. The threaded proximal portion 103 is arranged on the bone screw 100 such that, when the bone screw is installed within an intramedullary canal of a hand or foot bone, the threaded proximal portion 103 of the bone screw 100 aligns with and engages cancellous bone of one end of the intramedullary canal of the hand or foot bone.

In one embodiment, the thread 104 of the threaded distal portion 101 and the thread 112 of the threaded proximal portion 103 each form a cancellous-type bone threading to fully engage the bone at either end of the intramedullary canal. In this embodiment, the thread 104 and the thread 109 of the threaded center portion 102 form a cortical-type bone threading to fully engage the isthmus in the center of the intramedullary canal, which has a smaller diameter than either end of the intramedullary canal.

For example, as shown in FIG. 1, the cortical-type bone thread has a greater density of thread revolutions (e.g., smaller thread pitch) than the cancellous-type bone threading. The cancellous-type bone threading (e.g., the revolutions of the thread 104 and the revolutions of the thread 112) may have a greater pitch so that there is more bone purchase between the thread revolutions whereas the cortical-type bone threading (e.g., the revolutions of the thread 104 and the thread 109) may have a smaller pitch to enable more grip in harder bone.

In at least some examples, as shown in FIG. 1, an open end of the threaded proximal portion 103 may form a driving end 115 of the bone screw 100.

In one embodiment, the bone screw 100 may include means for a guide wire. For example, the bone screw 100 may be a cannulated screw with a hollow central shaft for a guide wire.

Figure 2:
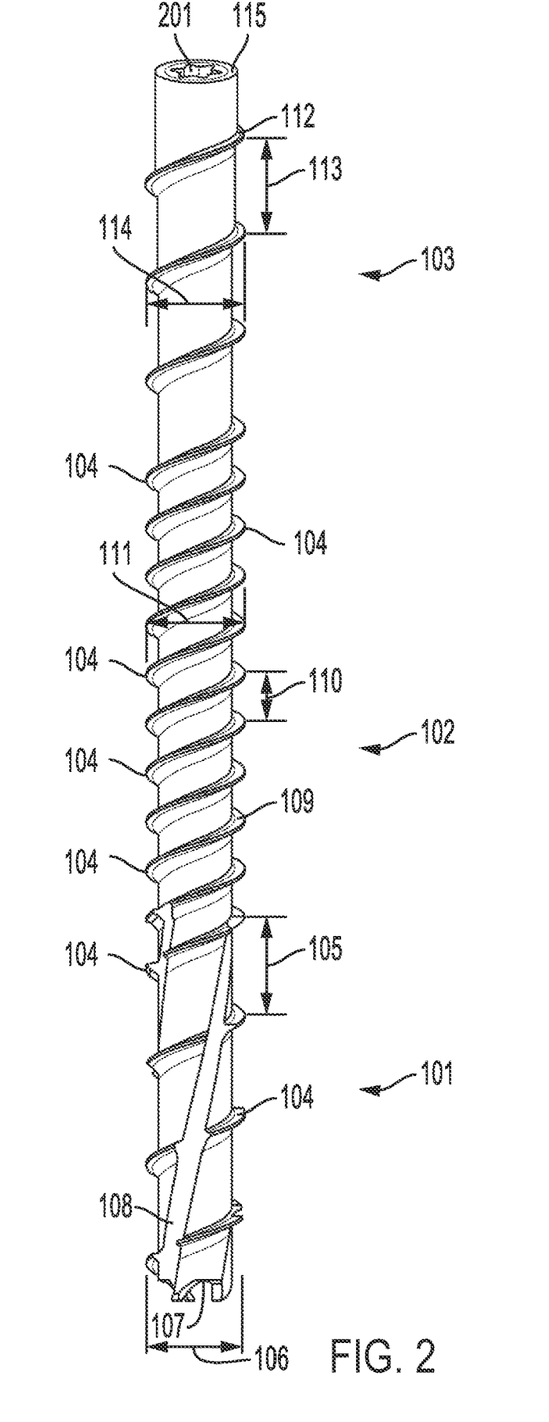
FIG. 2 illustrates a perspective view of the bone screw of FIG. 1 taken from an angle of a threaded proximal portion of the bone screw, according to an aspect of the present disclosure.
Figure 3:
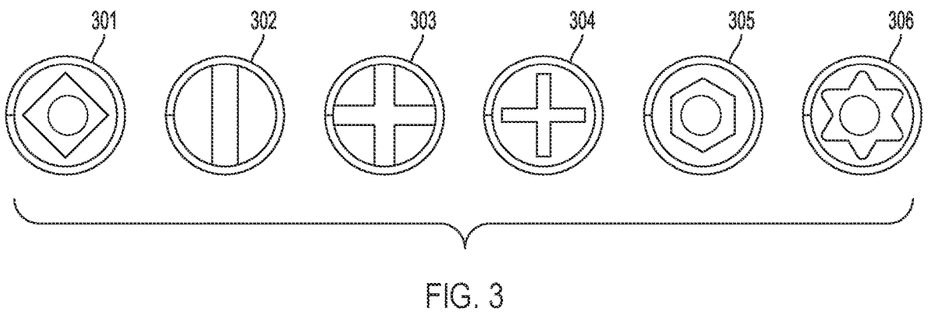
FIG. 3 illustrates example driving interfaces of the bone screw of FIG. 1, according to aspects of the present disclosure.

Referring now to FIG. 2, a perspective view of the example bone screw 100 is shown. As shown in FIG. 2, the open end of the threaded proximal portion 103 forms the driving end 115 of the bone screw 100. In one embodiment, the driving end 115 of the bone screw 100 may include an opening 201. The shape of the opening 201 corresponds to and engages with a driving device such as a screw driver or any other suitable device for driving the bone screw 100 during a surgery. FIG. 3 illustrates non-limiting examples of shapes for the opening 201. For example, the opening 201 may have the shape 301, the shape 302, the shape 303, the shape 304, the shape 305, or the shape 306, among other suitable shapes.

FIGS. 2 and 3 illustrate the driving end 115 as a female drive feature. In other examples, the driving end 115 may include a male drive feature. In such other examples, the male drive feature corresponds to a female drive feature of a suitable driving device such as a screw driver.

Figure 4:
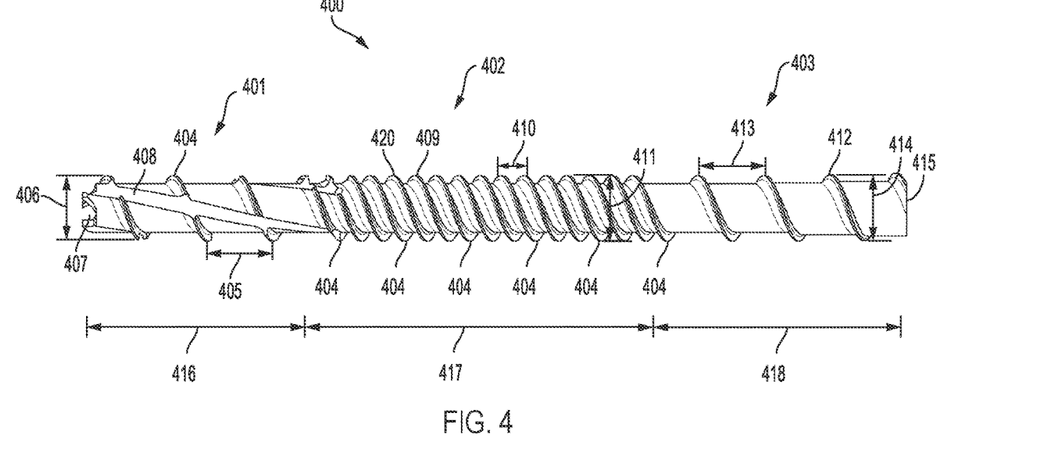
FIG. 4 illustrates a perspective view of a bone screw having a triple-threaded central portion in accordance with an embodiment of the present disclosure.

FIG. 4 is a perspective view of an example bone screw 400. As shown in FIG. 4, the bone screw 400 includes a threaded distal portion 401, a threaded center portion 402 and a threaded proximal portion 403. The threaded center portion 402 of the bone screw 400 is triple-threaded whereas the threaded center portion 102 of the example bone screw 100 is dual-threaded. Otherwise, in various aspects, the description of the example bone screw 100 above may likewise apply to the example bone screw 400.

The threaded distal portion 401 has a thread 404 with multiple revolutions within the threaded distal portion 401. In one embodiment, the threaded distal portion 401 is fully threaded with the thread 404.

In some aspects, the threaded distal portion 401 has a constant core diameter (not shown) throughout the threaded distal portion 401. In some aspects, the thread 404 has a constant outside diameter 406 throughout the threaded distal portion 401. In other aspects, the outside diameter 406 is not constant. For example, the outside diameter 406 can increase or decrease toward either end of the threaded distal portion 401.

In at least one embodiment, the bone screw 400 may have the same constant core diameter (not shown) throughout the bone screw 400 as that of the thread 404. For instance, the bone screw 400 may have the same constant core diameter throughout the threaded distal portion 401, the threaded central portion 402, and the threaded proximal portion 403. In one embodiment, the bone screw 400 may have the same constant outside diameter 406 throughout the bone screw 400 as that of the thread 404. For instance, the bone screw 400 may have the same constant outside diameter 406 throughout the threaded distal portion 401, the threaded central portion 402, and the threaded proximal portion 403.

In one embodiment, the thread 404 of the threaded distal portion 401 has a constant pitch 405. When the bone screw 400 is inserted within an intramedullary canal of a hand or foot bone the threaded distal portion 401 is arranged on the bone screw 400 such that the threaded distal portion 401 can engage cancellous bone within the intramedullary canal. As such, in at least some aspects, the constant pitch 405, the profile of the thread 404, the constant outside diameter 406, and/or a length 416 of the threaded distal portion 401 are adapted to fully engage cancellous bone on either end of an intramedullary canal a hand or foot bone, such as a metacarpal or a metatarsal.

In one embodiment, an open end 407 of the threaded distal portion 401 forms a leading end of the bone screw 401. For example, the threaded distal portion 401 can include self-tapping portion 408, which can help the bone screw 400 to better cut into a hand or foot bone.

In one embodiment, a surgeon might first examine a hand or foot bone of a patient to determine a suitable length, outside diameter, profile of threads and/or thread pitch of a bone screw 400. The suitable whole length 416, constant outside diameter 406, profile of the threads 404, and/or constant pitch 405 of the threaded distal portion 401 may then be determined on the basis of a specific hand or foot bone of a specific patient.

Returning to FIG. 4, the threaded center portion 402 includes multiple revolutions of the thread 404, multiple revolutions of a thread 409, and multiple revolutions of a thread 420. In one embodiment, the threaded center portion 402 is fully threaded with the thread 404, the thread 409, and the thread 420.

In one embodiment, the threaded center portion 402 has a constant core diameter (not shown) throughout the threaded center portion 402. In one embodiment, the thread 409 has a constant outside diameter 411 throughout the threaded center portion 402. In one embodiment, the constant outside diameter 411 of the thread 409 is equal to the constant outside diameter 406 of the thread 404.

In one embodiment, the core diameter of the threaded center portion 402 is not constant. For example, the core diameter of the threaded center portion 402 may increase or decrease toward either end of the threaded center portion 402.

In one embodiment, the bone screw 400 as a whole has a constant outside diameter equal to the constant outside diameter 411.

In at least one embodiment, the threaded center portion 402 has a constant pitch 410. The constant pitch 410 for the threaded center portion 402 is smaller than the constant pitch 405 of the threaded distal portion 401. As such, threaded center portion 402 has a greater density of the revolutions of the thread 404, the thread 409, and the thread 420 as compared to the density of the revolutions of the thread 404 in the threaded distal portion 401. In at least some aspects, the thread 409 may have a constant pitch equal to the constant pitch 405. In at least some aspects, the thread 420 may have a constant pitch equal to the constant pitch 405. In at least some aspects, both the thread 409 and the thread 420 each have a constant pitch equal to the constant pitch 405.

In various aspects, the constant pitch 410 for the threaded center portion 402 may be ½, ⅓, ¼, ⅕, ⅙, 1/7, ⅛, 1/9, 1/10, 1/11, 1/12, etc. of the constant pitch 405 of the threaded distal portion 401. For example, FIG. 4 shows that the constant pitch 410 for the threaded center portion 402 is ⅓ of the constant pitch 405 of the threaded distal portion 401. FIG. 4 further shows that the thread 404 is continuous between the threaded distal portion 401 and the threaded center portion 402. Stated differently, the thread 404 is a single thread that extends through both the threaded distal portion 401 and the threaded center portion 402.

Within the intramedullary canals of a hand or foot bone, such as a metacarpal or a metatarsal, the threaded center portion 402 of the bone screw 400 would align with and fully support cortical bone (i.e., isthmus) in the center.

The greater density of thread revolutions (e.g., smaller pitch) in the threaded center portion 402 as compared with the threaded distal portion 401 helps provide additional support for the bone screw 400 to secure the isthmus in the center of the intramedullary canal.

In one embodiment, the threaded distal portion 401 of the bone screw 400 can comprise any suitable quantity of thread revolutions that fit in the threaded distal portion 401. For example, the threaded distal portion 401 of the bone screw 400 can include 1, 2, 3, 4, 5, 6, 7, 8, 9, 10, etc. revolutions of the thread 404.

In one embodiment, the threaded center portion 402 of the bone screw 400 can include any suitable quantity of thread revolutions that fit in the threaded center portion 402. For example, the threaded center portion 402 of the bone screw 400 can include 6, 8, 10, 12, 14, 16, 18, 20, or more revolutions of the thread 404, the thread 409, and the thread 420.

In one embodiment, the threaded center portion 402 of the bone screw 400 may include 8 or more revolutions of the thread 404, the thread 409, and the thread 420.

In one embodiment, the threaded center portion 402 of the bone screw 400 may include 10 or more revolutions of the thread 404, the thread 409, and the thread 420.

In one embodiment, the threaded center portion 402 of the bone screw 400 may include 12 or more revolutions of the thread 404, the thread 409, and the thread 420.

In one embodiment, the threaded center portion 402 of the bone screw 400 may include 16 or more revolutions of the thread 404, the thread 409, and the thread 420.

In at least some aspects, the parameters of the threaded center portion 402—the whole length 417, the constant outside diameter 411, the profile of the thread 404, the thread 409, and the thread 420, and/or the constant pitch 410—are adapted to fit within an intramedullary canal and fully engage cortical bone (i.e., isthmus) of the center of a hand or foot bone, such as a metacarpal or a metatarsal. For example, a surgeon might first examine a related hand or foot bone of a patient to determine a suitable length, outside diameter, profile of threads and/or thread pitch of a bone screw. The suitable whole length 417, constant outside diameter 411, profile of the threads 409, and/or constant pitch 410 of the threaded center portion 402 may then be determined on the basis of a specific hand or foot bone of a specific patient.

As shown in FIG. 4, the bone screw 400 also includes the threaded proximal portion 403. The threaded proximal portion 403 includes multiple revolutions of a thread 412. In one embodiment, the threaded proximal portion 403 is fully threaded with the thread 412.

In at least some aspects, the thread 412 is the thread 404. Stated differently, in such aspects, the thread 404 is a single, continuous thread that extends throughout the threaded distal portion 401, the threaded center portion 402, and the threaded proximal portion 403.

In one embodiment, the threaded proximal portion 403 has a constant core diameter (not shown) throughout the threaded proximal portion 403. In one embodiment, the thread 412 has a constant outside diameter 414 throughout the threaded proximal portion 403. In one embodiment, the constant outside diameter 414 is equal to the constant outside diameter 411 of the threaded center portion 402.

In another embodiment, the core diameter (not shown) of the threaded proximal portion 403 is not constant throughout the threaded proximal portion 403. For example, the core diameter of the threaded proximal portion 403 can increase or decrease toward either end of the threaded proximal portion 403.

In one embodiment, the thread 412 has a constant outside diameter 414 throughout the threaded proximal portion 403. In one embodiment, the constant outside diameter 414 for the threaded proximal portion 403, the constant outside diameter 411 for the threaded center portion 402, and the constant outside diameter 406 for the threaded distal portion 401 are all equal. As such, the bone screw 400 has a uniform outside diameter throughout in this embodiment.

In another embodiment, the outside diameter 414 of the thread 412 is not constant throughout the threaded proximal portion 403. For example, the outside diameter 414 of the threaded proximal portion 403 can increase or decrease toward either end of the threaded proximal portion 403.

In one embodiment, the thread 412 of the threaded proximal portion 403 has a constant pitch 413. In some aspects, the constant pitch 413 for the threaded proximal portion 403 is equal to the constant pitch 405 of the thread 404 of the threaded distal portion 401.

In at least some embodiments, the constant pitch 413, the constant pitch 405 and the constant pitch 410 enable the thread 404 to extend continuously through the threaded distal portion 401, the threaded center portion 402, and the threaded proximal portion 403.

In various aspects, the whole length 418, the constant outside diameter 414, the profile of the thread 412, and/or the constant pitch 413 of the threaded proximal portion 403 can be adapted to fit within an intramedullary canal and fully engage cancellous bone of either end of a hand or foot bone, such as a metacarpal or a metatarsal. The threaded proximal portion 403 is arranged on the bone screw 400 such that, when the bone screw is installed within an intramedullary canal of a hand or foot bone, the threaded proximal portion 403 of the bone screw 400 aligns with and engages cancellous bone of one end of the intramedullary canal of the hand or foot bone.

In one embodiment, the thread 104 of the threaded distal portion 401 and the thread 412 of the threaded proximal portion 403 each form a cancellous-type bone threading to fully engage the bone at either end of the intramedullary canal. In this embodiment, the thread 104, the thread 409, and the thread 420 of the threaded center portion 402 form a cortical-type bone thread to fully engage the isthmus in the center of the intramedullary canal, which has a smaller diameter than either end of the intramedullary canal.

For example, as shown in FIG. 1, the cortical-type bone thread has a greater density of thread revolutions (e.g., smaller thread pitch) than the cancellous-type bone threading. The cancellous-type bone threading (e.g., the revolutions of the thread 404 and the revolutions of the thread 412) may have a greater pitch so that there is more bone purchase between the thread revolutions whereas the cortical-type bone threading (e.g., the revolutions of the thread 104, the thread 409, and the thread 412) may have a smaller pitch to enable more grip in harder bone.

In some examples, as shown in FIG. 4, an open end of the threaded proximal portion 403 may form a driving end 415 of the bone screw 400.

In one embodiment, the bone screw 400 may include means for a guide wire. For example, the bone screw 400 may be a cannulated screw with a hollow central shaft for a guide wire.

Figure 5:
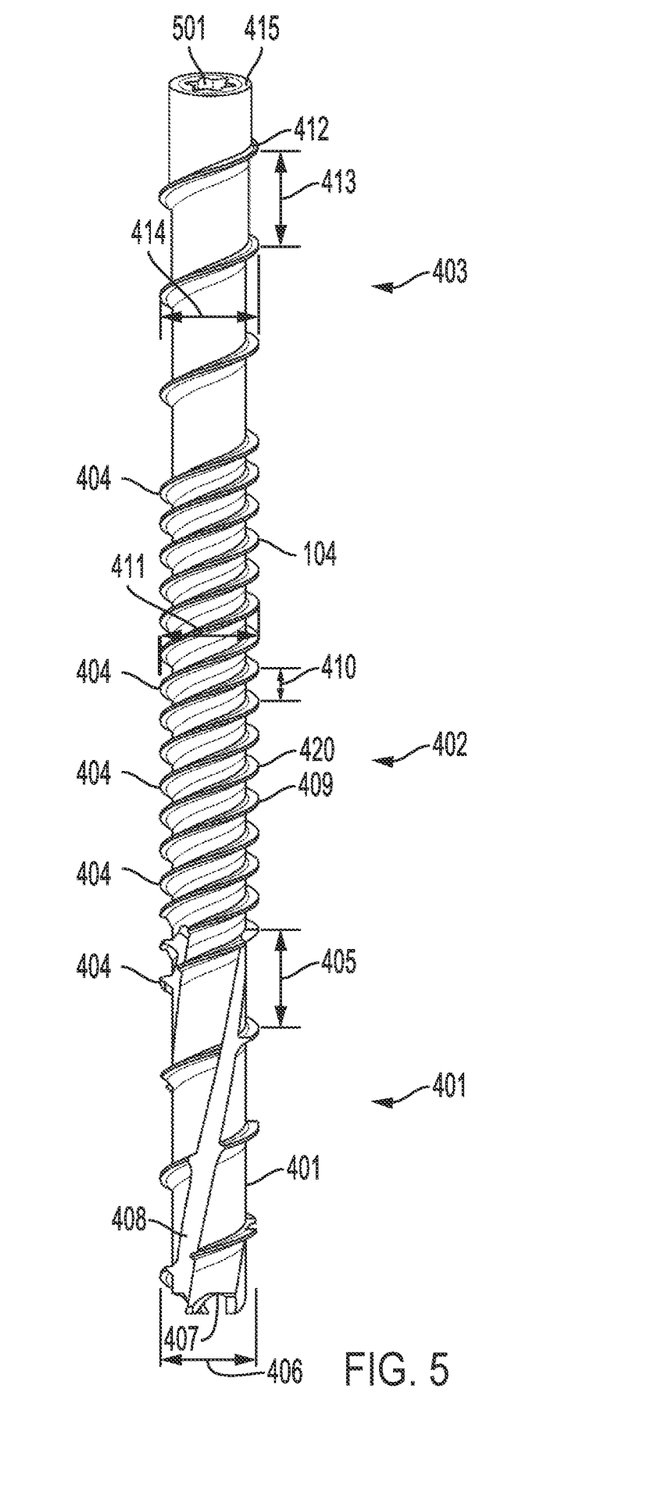
FIG. 5 illustrates a perspective view of the bone screw of FIG. 4 taken from an angle of a threaded proximal portion of the bone screw, according to an aspect of the present disclosure.

Referring now to FIG. 5, a perspective view of the same device as FIG. 4 is shown. As stated above, the open end of the threaded proximal portion 403 may form a driving end 415 of the bone screw 400. In one embodiment, the driving end 415 of the bone screw 400 may include an opening 501. The shape of the opening 501 may correspond to and engage with a driving device such as a screw driver or any other devices applicable to drive the bone screw 400 during a surgery.

Figure 6:
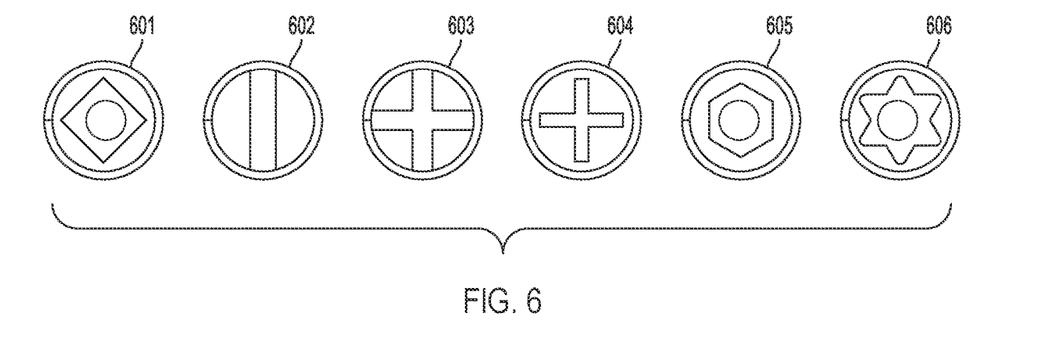
FIG. 6 illustrates example driving interfaces of the bone screw of FIG. 4, according to aspects of the present disclosure.

Referring now to FIG. 6, non-limiting examples of shapes for the opening 501 are shown. For example, the opening 501 may have a shape 601, a shape 602, shape 603, a shape 604, the shape 605, a shape 606 or other suitable shapes.

FIGS. 5 and 6 illustrate the driving end 415 as a female drive feature. In other examples, the driving end 415 may include a male drive feature. In such other examples, the male drive feature corresponds to a female drive feature of a suitable driving device such as a screw driver.

Figure 7:
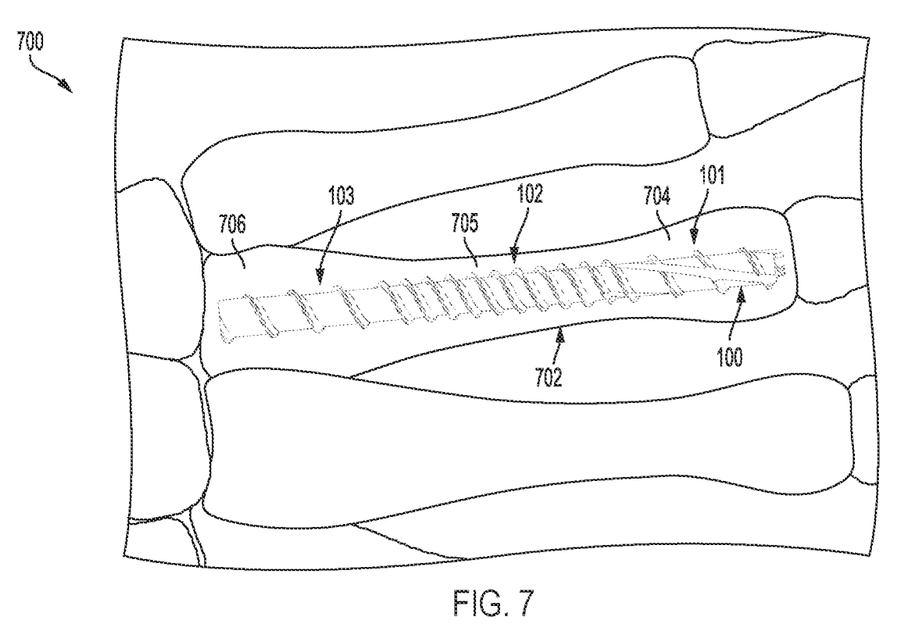
FIG. 7 illustrates the bone screw of FIG. 1 installed within an intramedullary canal of a patient's metacarpal, according to an aspect of the present disclosure.

FIG. 7 illustrates a portion of the bones of a hand 700 of a patient showing the example bone screw 100 installed within an intramedullary canal of a metacarpal 702 of the patient. Consistent with the preceding description, the threaded distal portion 101 is positioned within a first bone section 704 of the metacarpal 702, the first bone section 704 being a cancellous bone section of the metacarpal 702. The threaded center portion 102 is positioned within a second bone section 705 of the metacarpal 702, the second bone section 705 being a cortical (i.e. isthmus) bone section of the metacarpal 702. The threaded proximal portion 103 is positioned within a third bone section 706 of the metacarpal 702, the third bone section 706 being a cancellous bone section of the metacarpal 702.

As described above, the threaded distal portion 101, the threaded central portion 102, and the threaded proximal portion 103 are each constructed to fully engage their respective bone section 704, 705, 706. In particular, the threaded central portion 102 includes at least one additional thread, and thus a higher density of thread revolutions, compared to the threaded distal portion 101 and the threaded proximal portion 103 to help support the isthmus (i.e. cortical bone) in the center of the metacarpal 702. As such, stability of the bone screw 100 within the intramedullary canal of the metacarpal 702 is improved as compared to typical bone screws.

Figure 8:
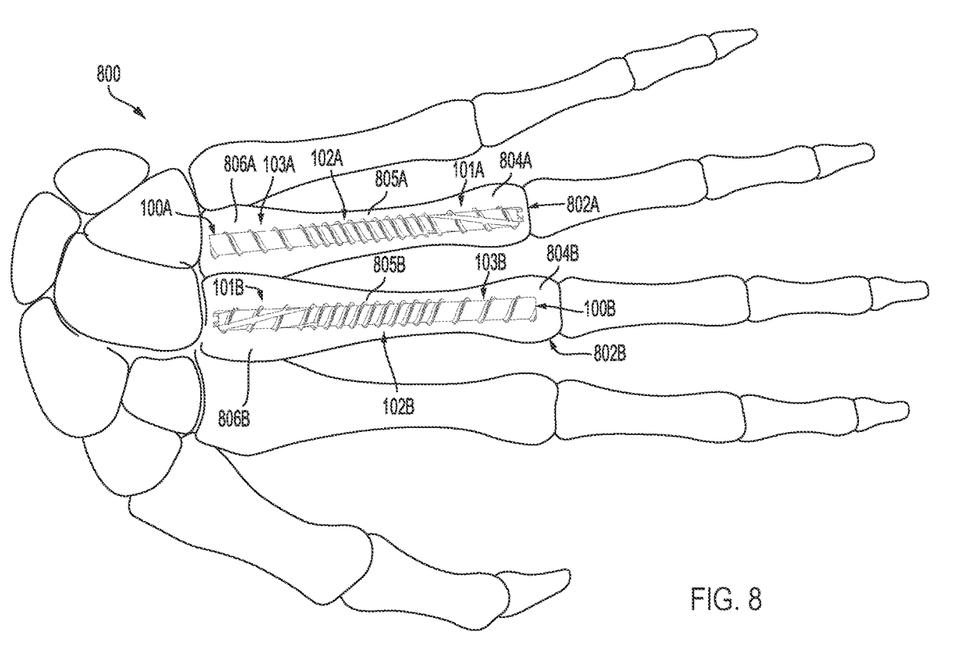
FIG. 8 illustrates two bone screws installed in opposite orientations within their respective metacarpals, according to an aspect of the present disclosure.

FIG. 8 illustrates bones of a hand 800 of a patient including a metacarpal 802A and a metacarpal 802B. An example bone screw 100A is installed within the metacarpal 802A and an example bone screw 100B is installed within the metacarpal 802B. Each of the bone screw 100A and the bone screw 100B are examples of the bone screw 100 described above.

The threaded distal portion 101A of the bone screw 100A is positioned within a first bone section 804A of the metacarpal 802A, the first bone section 804A being a cancellous bone section of the metacarpal 802A. The threaded center portion 102A is positioned within a second bone section 805A of the metacarpal 802A, the second bone section 805A being a cortical (i.e. isthmus) bone section of the metacarpal 802A. The threaded proximal portion 103A is positioned within a third bone section 806A of the metacarpal 802A, the third bone section 806A being a cancellous bone section of the metacarpal 802A.

The threaded distal portion 101B of the bone screw 100B is positioned within a third bone section 806B of the metacarpal 802B, the third bone section 806B being a cancellous bone section of the metacarpal 802B. The threaded center portion 102B is positioned within a second bone section 805B of the metacarpal 802B, the second bone section 805B being a cortical (i.e. isthmus) bone section of the metacarpal 802B. The threaded proximal portion 103B is positioned within a first bone section 804B of the metacarpal 802B, the first bone section 804B being a cancellous bone section of the metacarpal 802B.

The orientations of the bone screw 100A and the bone screw 100B within the metacarpal 802A and the metacarpal 802B, respectively, illustrate that the example bone screw 100 may be installed in either an antegrade or retrograde manner into an intramedullary canal.

The present disclosure also provides a method for treating a bone fracture or osteotomy of a patient by using the above-described bone screws (e.g., the bone screw 100 or 400). An example method may include inserting into a foot or hand bone of a patient, through an incision in a foot or a hand of the patient, a bone screw (e.g., the bone screw 100). The bone screw 100 includes a threaded distal portion 101, a threaded center portion 102, and a threaded proximal portion 103. The threaded distal portion 101 is configured and adapted for insertion into an intramedullary canal of a first cancellous bone section (e.g., the bone section 704) of the foot or the hand bone. The threaded center portion 102 is configured and adapted for insertion into the intramedullary canal of an isthmus bone section (e.g., the bone section 705) of the foot or the hand bone. The threaded proximal portion 103 is configured and adapted for insertion into the intramedullary canal of a second cancellous bone section (e.g., the bone section 706) of the foot or the hand bone. Each of the threaded distal portion 101 and the threaded proximal portion 103 has a first constant diameter and a first constant pitch, and the threaded center portion 102 has a second constant diameter and a second constant pitch throughout the threaded center portion 102. The second constant diameter is the same as the first constant diameter, and the second constant pitch is smaller than the first constant pitch.

The method may also include adjusting the position of the bone screw 100 within the intramedullary canal so that the threaded proximal portion 103 and the threaded distal portion 101 of the bone screw 100 engage cancellous bones of either end of the foot or the hand bone (e.g., within the bone section 704 or the bone section 706), and the threaded center portion 102 of the bone screw 100 engages an isthmus (e.g., within the bone section 705), in the center of the foot or the hand bone.

In one embodiment, the bone screw 100 may be inserted in either an antegrade or retrograde manner through a head of a hand or foot bone. In another embodiment, the bone screw 100 may be inserted over a guide wire during insertion into the hand or foot bone. For example, a surgeon may insert a guide wire into the bone to reduce the fracture, drill a hole into the bone over the guide wire, and then insert the bone screw 100 over the guide wire and into the bone to the desired depth. The guide wire may then be removed.

It is believed that the present disclosure includes many other embodiments that may not be herein described in detail, but would nonetheless be appreciated by those skilled in the art from the disclosures made. Accordingly, this disclosure should not be read as being limited only to the foregoing examples or only to the designated embodiments.

What is claimed is:

1. A bone screw for intramedullary fixation of hand or foot bones, comprising:
    a threaded distal portion including a first thread, the threaded distal portion having a first constant outer thread diameter and a first constant pitch throughout the threaded distal portion, wherein an open end of the threaded distal portion forms a leading end of the bone screw;
    a threaded center portion including the first thread and a second thread, the threaded center portion having a second constant outer thread diameter and a second constant pitch throughout the threaded center portion, wherein the second constant outer thread diameter is the same as the first constant outer thread diameter, and the second constant pitch is smaller than the first constant pitch; and
    a threaded proximal portion including the first thread, the threaded proximal portion having the first constant outer thread diameter and the first constant pitch throughout the threaded proximal portion, wherein an open end of the threaded proximal portion forms a driving end of the bone screw, and
    wherein the first thread has the first constant outer thread diameter and the first constant pitch throughout the threaded distal portion, the threaded center portion, and the threaded proximal portion.

2. The bone screw of claim 1, wherein the bone screw is headless.

3. The bone screw of claim 1, wherein the threaded distal portion, the threaded center portion and the threaded proximal portion are fully threaded.

4. The bone screw of claim 1, wherein the second constant pitch is one half of the first constant pitch.

5. The bone screw of claim 1, wherein the second constant pitch is one third of the first constant pitch.

6. The bone screw of claim 1, wherein the threaded center portion of the bone screw includes at least six thread revolutions.

7. The bone screw of claim 1, wherein the threaded center portion of the bone screw includes at least eight thread revolutions.

8. The bone screw of claim 1, wherein the threaded center portion of the bone screw includes at least ten thread revolutions.

9. The bone screw of claim 1, wherein each of the threaded distal portion and the threaded proximal portion of the bone screw includes at least three thread revolutions.

10. The bone screw of claim 1, wherein at least part of the threaded distal portion of the bone screw is self-tapping.

11. The bone screw of claim 1, wherein the bone screw is configured for intramedullary fixation of metacarpals or metatarsals.

12. The bone screw of claim 1, wherein the first constant outer thread diameter of the bone screw is sized such that the first constant outer thread diameter of the bone screw fits within an intramedullary canal of a hand or foot bone.

13. The bone screw of claim 12, wherein the hand or foot bone is either a metacarpal or a metatarsal.

14. The bone screw of claim 13, wherein the threaded proximal portion and the threaded distal portion of the bone screw engage cancellous bones of either end of the metacarpal or the metatarsal, and the threaded center portion of the bone screw engages an isthmus, in the center of the metacarpal or the metatarsal.

15. The bone screw of claim 1, wherein the threaded center portion includes more than two threads.

16. A bone screw for a metacarpal or a metatarsal, comprising:
    a threaded distal portion configured and adapted for insertion into an intramedullary canal of a first bone section of the metacarpal or the metatarsal;
    a threaded center portion configured and adapted for insertion into the intramedullary canal of a second bone section of the metacarpal or the metatarsal; and
    a threaded proximal portion configured and adapted for insertion into the intramedullary canal of a third bone section of the metacarpal or the metatarsal, wherein each of the threaded distal portion and the threaded proximal portion has a first constant outer thread diameter and a first constant pitch, wherein the threaded center portion has a second constant outer thread diameter and a second constant pitch throughout the threaded center portion, and wherein the second constant outer thread diameter is the same as the first constant outer thread diameter, and the second constant pitch is smaller than the first constant pitch.

17. The bone screw of claim 16, wherein the first bone section and the third bone section are cancellous bone sections of the metacarpal or the metatarsal.

18. The bone screw of claim 16, wherein the second bone section is an isthmus bone section of the metacarpal or the metatarsal.

\* \* \* \* \*